(12) United States Patent
Behnke et al.

(10) Patent No.: US 7,117,816 B2
(45) Date of Patent: Oct. 10, 2006

(54) HEATED PET BED

(75) Inventors: Wendy Behnke, Appleton, WI (US); Elizabeth Bell, Appleton, WI (US); Jim Cotter, Waupaca, WI (US); Daniel A. Heuer, Fremont, WI (US); Bruce Siebers, Kimberly, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 35 days.

(21) Appl. No.: 10/880,759

(22) Filed: Jun. 30, 2004

(65) Prior Publication Data

US 2006/0000415 A1    Jan. 5, 2006

(51) Int. Cl.
*A01K 29/00* (2006.01)

(52) U.S. Cl. .......................... 119/28.5; 5/421
(58) Field of Classification Search ............... 119/28.5; 5/421
See application file for complete search history.

(56) References Cited

U.S. PATENT DOCUMENTS

| | | | |
|---|---|---|---|
| 3,125,663 A | | 3/1964 | Hoffman |
| 4,064,835 A | | 12/1977 | Rabenbauer |
| 4,303,074 A | | 12/1981 | Bender |
| 4,332,214 A | | 6/1982 | Cunningham |
| 4,366,804 A | * | 1/1983 | Abe ..................... 126/263.02 |
| 4,516,564 A | * | 5/1985 | Koiso et al. ........... 126/263.02 |
| 4,591,694 A | | 5/1986 | Phillips |
| 4,899,693 A | | 2/1990 | Arnold |
| 4,995,126 A | * | 2/1991 | Matsuda ....................... 5/421 |
| 5,025,777 A | | 6/1991 | Hardwick |
| 5,092,271 A | | 3/1992 | Kleinsasser |
| 5,324,911 A | | 6/1994 | Cranston |
| 5,371,340 A | | 12/1994 | Stanfield |
| 5,425,975 A | | 6/1995 | Koiso et al. |
| 5,469,592 A | * | 11/1995 | Johnson ......................... 5/654 |
| 5,653,741 A | | 8/1997 | Grant |
| 5,702,375 A | * | 12/1997 | Angelillo et al. ........... 604/358 |
| 5,715,772 A | | 2/1998 | Kamrath et al. |
| 5,724,911 A | | 3/1998 | McAlister |
| 5,730,721 A | * | 3/1998 | Hyatt et al. ................. 604/500 |
| 5,975,074 A | * | 11/1999 | Koiso et al. ................. 126/204 |
| 6,078,026 A | | 6/2000 | West |
| 6,084,209 A | | 7/2000 | Reusche et al. |

(Continued)

FOREIGN PATENT DOCUMENTS

CA          1261908 A          9/1989

(Continued)

*Primary Examiner*—Teri Pham Luu
*Assistant Examiner*—Kimberly S. Smith
(74) *Attorney, Agent, or Firm*—Schwegman, Lundberg, Woessner, & Kluth, P.A.

(57) ABSTRACT

The present invention relates to a pet bed that includes a heating layer which is formed of an enclosure and a heating composition sealed inside the enclosure. The enclosure includes a gas-permeable section such that the heating composition generates heat when a gas is received through the gas-permeable section. The pet bed further includes (i) a liner attached to the heating layer to engage a pet as the pet lies on the pet bed; (ii) a conforming layer attached to the heating layer such that the conforming layer conforms to the shape of the pet as the pet lies on the pet bed; and/or (iii) a backing layer attached to the heating layer such that the backing layer restricts movement of the pet bed. The enclosure may further include a cover over the gas-permeable section such that the heating composition generates heat when the cover is removed from the enclosure.

20 Claims, 5 Drawing Sheets

U.S. PATENT DOCUMENTS

| | | | |
|---|---|---|---|
| 6,127,294 | A | 10/2000 | Koiso |
| 6,158,427 | A * | 12/2000 | McGuire et al. ....... 126/263.01 |
| 6,189,487 | B1 | 2/2001 | Owen et al. |
| 6,237,531 | B1 | 5/2001 | Peeples et al. |
| 6,409,746 | B1 * | 6/2002 | Igaki et al. ................. 607/109 |
| 6,488,561 | B1 | 12/2002 | Weiner |
| 6,553,935 | B1 | 4/2003 | Penner |
| 6,893,453 | B1 * | 5/2005 | Agarwal et al. ............ 607/108 |
| 2003/0115670 | A1 | 6/2003 | Antinoro |
| 2004/0116990 | A1 | 6/2004 | Agarwal et al. |
| 2004/0217325 | A1 * | 11/2004 | Usui et al. .................... 252/70 |

FOREIGN PATENT DOCUMENTS

| | | |
|---|---|---|
| DE | 10110080 A1 | 9/2002 |
| EP | 0370600 A1 | 5/1990 |
| EP | 0376490 A1 | 7/1990 |
| EP | 0885558 A1 | 12/1998 |
| EP | 1121912 A2 | 8/2001 |
| GB | 2030437 A | 4/1980 |
| GB | 2342266 A | 5/2000 |
| GB | 2393732 | 4/2004 |
| JP | 02142561 A | 5/1990 |
| WO | WO-9701313 A2 | 1/1997 |
| WO | WO-0033645 A1 | 6/2000 |

* cited by examiner

HEATED PET BED

FIELD

The present invention relates to a pet bed and more particularly to a heated pet bed that transfers heat to a pet when the pet is lying on the bed.

BACKGROUND

Many pets suffer from a variety of maladies, such as stiffness, muscle pain, arthritis, lumbago, rheumatism and neuralgia (among others). One way to treat a pet that has these types of maladies is to provide heat to the pet. Some known heat-treating methods include direct application of heat to the body using items such as a towel, jelly and/or paste.

One concern with such heat-treating methods relates to the ability to control the amount of heat that is applied to the pet, especially since pets are incapable of providing verbal feedback as to the amount of heat that they are receiving. A burn could result if too much heat is applied to a pet, and a pet may receive relatively ineffective therapy if too little heat is applied. Another concern with these types of heat-treating methods relates to their ability to apply heat for extended periods of time.

Pet owners commonly have their pets sleep in an environment where no heating facilities are available. As an example, pets often sleep in unheated garage spaces that are near their owner's home. A pet bed is typically used to keep pets warm as they sleep and/or to provide heat therapy to an ailing pet.

Some conventional pet beds include a thermoelectric device that generates heat within the pet bed. One of the drawbacks with such pet beds is that the thermoelectric devices require electricity to generate heat. Since electricity is not available in many locations, bulky, expensive and environmentally unfriendly batteries are often required to supply the necessary electricity.

Accordingly, there is a need for a pet bed that applies heat to a pet without using electricity. The pet bed should also be capable of maintaining a safe temperature for an extended period of time.

SUMMARY OF THE INVENTION

The present invention relates to a pet bed that generates heat by an exothermic reaction which takes place within the pet bed. The rate of the exothermic reaction is easily controlled such that the temperature of the pet bed can be readily regulated. The pet bed is also easily manufactured and supplies heat for an extended period of time without using electricity.

In one aspect, the present invention relates to a pet bed that includes a heating layer which is formed of an enclosure and a heating composition sealed inside the enclosure. The enclosure includes a gas-permeable section such that the heating composition generates heat when a gas is received through the gas-permeable section of the enclosure In some embodiments, the pet bed further includes a liner that is attached to the heating layer. The liner engages a pet as the pet lies on the pet bed.

In other embodiments, the pet bed further includes a conforming layer that is attached to the heating layer. The conforming layer conforms to the shape of a pet as the pet lies on the pet bed.

In still other embodiments, the pet bed further includes a backing layer that is attached to the heating layer. The backing layer restricts movement of the pet bed relative to a surface where the pet bed is situated.

In another aspect, the present invention relates to a pet bed that includes a heating layer which is formed of an enclosure and a heating composition sealed inside the enclosure. The enclosure includes a gas-permeable section such that the heating composition generates heat when a gas is received through the gas-permeable section of the enclosure. The pet bed further includes a conforming layer that is attached to the heating layer and a liner that is attached to the conforming layer. The conforming layer conforms to the shape of a pet as the pet lies on the pet bed and the liner engages the pet as the pet lies on the pet bed. The pet bed further includes a backing layer that is attached to the heating layer. The backing layer restricts movement of the pet bed relative to a surface where the pet bed is situated In still another aspect, the present invention relates to a pet bed that includes a heating layer which is formed of an enclosure and a heating composition sealed inside the enclosure. The enclosure includes a gas-permeable section and a cover positioned over the gas-permeable section such that the heating composition generates heat when the cover is removed from the enclosure and a gas is received through the gas-permeable section of the enclosure. The pet bed further includes (i) a liner attached to the heating layer to engage a pet as the pet lies on the pet bed; (ii) a conforming layer attached to the heating layer such that the conforming layer conforms to the shape of the pet as the pet lies on the pet bed; and/or (iii) a backing layer attached to the heating layer such that the backing layer restricts movement of the pet bed relative to a surface where the pet bed is situated.

In some embodiments, the enclosure of the heating layer may further include at least one additional gas-permeable section such that at least one additional cover is positioned over each of the gas-permeable sections of the enclosure. In addition, the cover may be attached to the enclosure within an opening in the liner, conforming layer or backing layer.

The purposes and features of the present invention will be set forth in the description that follows. Additional features of the invention will be realized and attained by the product and processes particularly pointed out in the written description and claims hereof, as well as from the appended drawings.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the invention.

BRIEF DESCRIPTION OF THE DRAWINGS

The present invention will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

DETAILED DESCRIPTION OF THE INVENTION

In the following detailed description, reference is made to the accompanying drawings, which show specific embodiments in which the invention may be practiced. These embodiments are described in sufficient detail to enable those skilled in the art to practice the invention. It is to be understood that other embodiments may be utilized and structural changes made, such that the following detailed description is not to be taken in a limiting sense.

Figure 1:
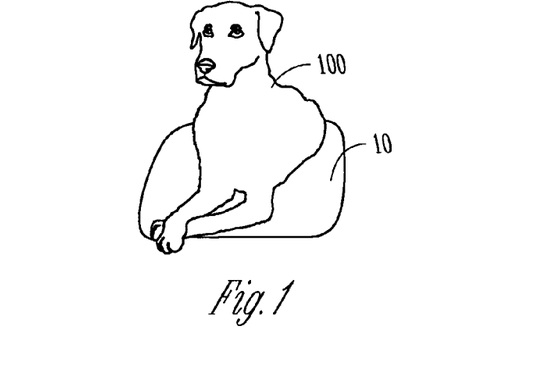
FIG. 1 illustrates a dog lying on an example pet bed.
Figure 2:
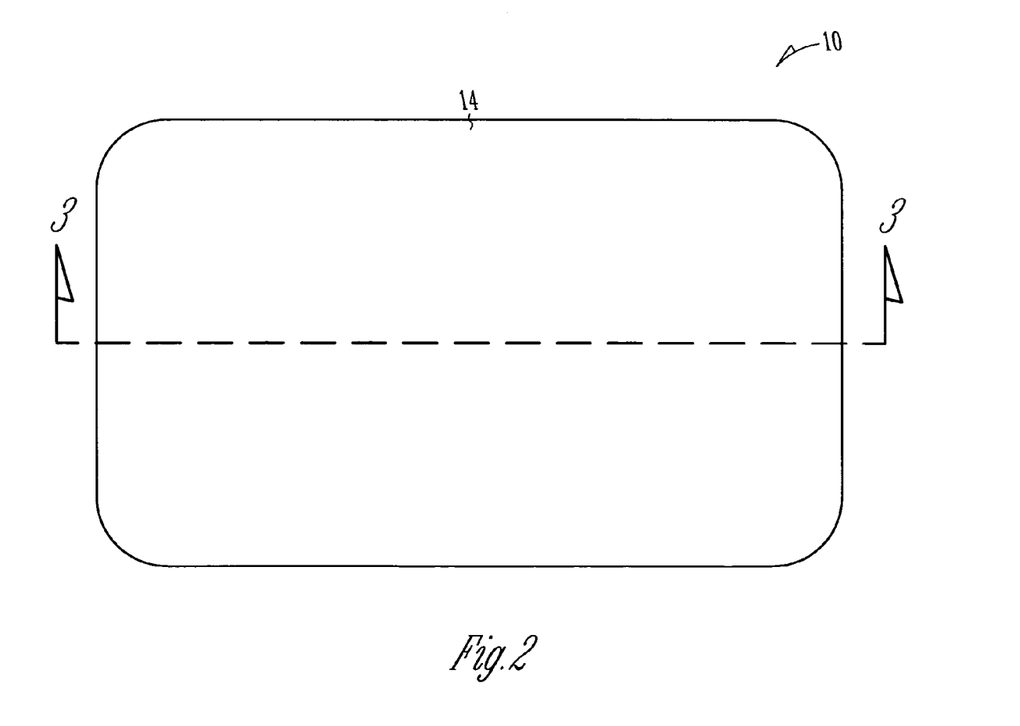
FIG. 2 illustrates a top view of the pet bed shown in FIG. 1.

FIG. 1 illustrates a dog 100 lying on an example pet bed 10. FIG. 2 illustrates a top view of the pet bed 10 shown in FIG. 1.

Figure 3:
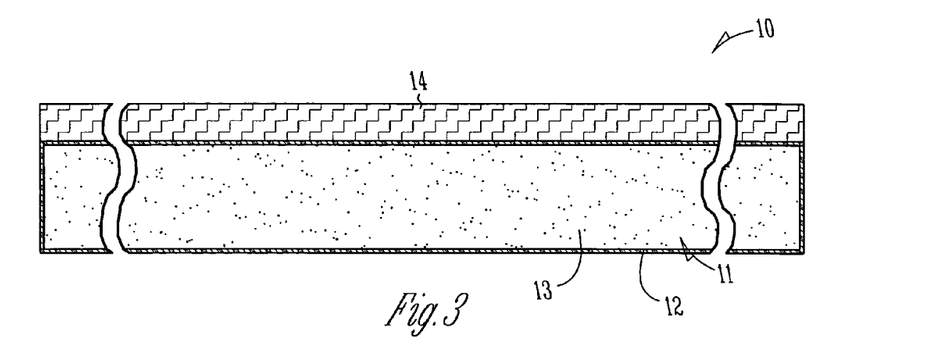
FIG. 3 is a section view illustrating an example embodiment of the pet bed shown in FIG. 2 taken along line 3—3.

As shown in FIG. 3, the pet bed 10 includes a heating layer 11 that is formed of an enclosure 12 and a heating composition 13 sealed inside the enclosure 11. The pet bed 10 further includes a liner 14 that is attached to the heating layer 11 to engage a pet as the pet lies on the pet bed 10.

In the illustrated example embodiment, the entire enclosure 12 is made from a gas-permeable material such that the heating composition 13 generates heat when a gas, such as oxygen contained in ambient air, is received through the enclosure 12. In other embodiments, the enclosure 12 may include one or more gas-permeable sections such that a gas is delivered to the heating composition 13 through the gas-permeable sections of the enclosure 12. The enclosure 12 may be a polyethylene film (among other materials) with any gas-permeable sections formed of polyethylene, polypropylene and/or nylon nonwoven fabrics (among other materials).

The pet bed 10 may be stored in a hermetic environment (e.g., a sealed bag, not shown) such that the heating composition 13 remains inactivate until the pet bed 10 is removed from the hermetic environment. Once the pet bed 10 is removed from the hermetic environment and exposed to air, an exothermic reaction takes place. The exothermic reaction generates heat that causes the temperature of the pet bed 10 to rise.

The rate at which the exothermic reaction takes place is determined by the amount of heating composition 13 and the amount of air that feeds the exothermic reaction. Increasing the rate at which the exothermic reaction takes place causes the temperature of the pet bed to rise but reduces the duration of the exothermic reaction.

The exothermic reaction within the pet bed 10 maintains the temperature of the pet bed 10 at substantially the same level over a relatively long period of time. As an example, the exothermic reaction within the enclosure 12 may generate sufficient heat to raise the temperature of the pet bed 10 to anywhere between 38 and 44 degrees C. for anywhere between 6–40 hours.

In the embodiment illustrated in FIG. 3, the liner 14 and the heating layer 11 are the same size such that the liner 14 may be bonded around its perimeter to the perimeter of the enclosure 12 by such means as adhesion, melt-bonding, ultrasonic or sewing (among others). It should be noted that the heating layer 11 and the liner 14 may be bonded at other locations besides their perimeters, especially when the heating layer 11 and the liner 14 are different sizes.

The liner 14 may be made from a material that is moisture-proof, comfortable, non-toxic, low cost, gas-permeable and/or hygienic. Some example materials that may be used for the liner 14 include nonwovens, breathable films, polyethylene, bonded carded web, cellulose (among other materials). In some embodiments, the liner 14 may be made from a combination of materials and/or formed of multiple layers that are made of the same material or different materials.

Any conventional heating composition may be used to induce an exothermic reaction in the presence of a gas such as air. Some example heating compositions include iron powder as the main active ingredient.

Figure 4:
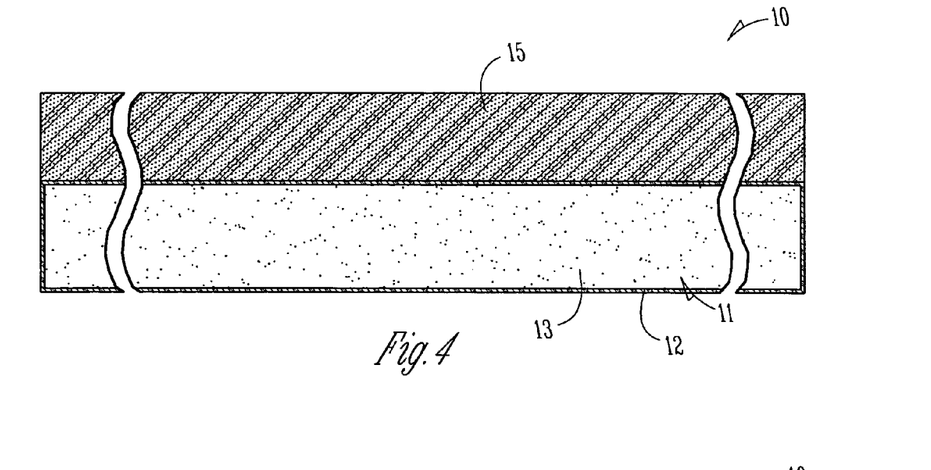
FIG. 4 is a section view that is similar to FIG. 3 illustrating another example embodiment of the pet bed shown in FIG. 2.

FIG. 4 illustrates another example embodiment for pet bed 10. The pet bed 10 includes a heating layer 11 that is formed of an enclosure 12 and a heating composition 13 sealed inside the enclosure 12. The heating composition 13 generates heat when a gas (e.g., air) is received through one or more gas-permeable sections of the enclosure 12. In the illustrated example embodiment, the entire enclosure 12 is made from a gas-permeable material.

The pet bed 10 further includes a conforming layer 15 that is attached to the heating layer 11. The conforming layer 15 conforms to the shape of a pet as the pet lies on the pet bed 10.

In the embodiment illustrated in FIG. 4, the conforming layer 15 and the heating layer 11 are the same size such that the conforming layer 15 may be bonded around its perimeter to the perimeter of the enclosure 12 by such means as adhesion, melt-bonding, ultrasonic or sewing (among others). It should be noted that the heating layer 11 and the conforming layer 15 may be bonded at other locations besides their perimeters, especially when the heating layer 11 and the conforming layer 15 are different sizes.

Figure 5:
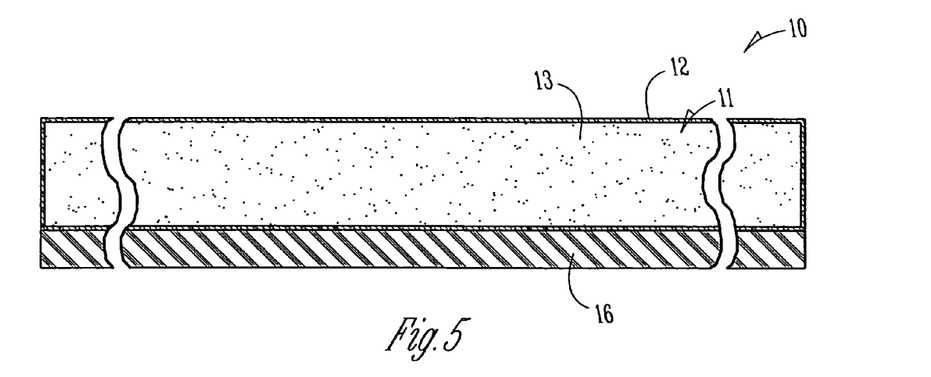
FIG. 5 is a section view that is similar to FIGS. 3–4 illustrating another example embodiment of the pet bed shown in FIG. 2.

The conforming layer 15 may be made from a material that is comfortable, non-toxic, low cost and/or hygienic. Some example materials that may be used for conforming layer 15 include different types of foam, high loft nonwovens, nonwovens composites such as co-form, rubber, springs, (among other materials). In some embodiments, the conforming layer 15 may be made from a combination of materials and/or formed of multiple layers that are made of the same material or different materials. In addition, the conforming layer 15 may include an enclosure (not shown) that contains materials such as cedar, feathers down, air, foam pellets, hay and organic bedding material (among other materials). FIG. 5 illustrates another example embodiment for pet bed 10. The pet bed 10 includes a heating layer 11 that that is formed of an enclosure 12 and a heating composition 13 sealed inside the enclosure 12. The heating composition 13 generates heat when a gas (e.g., air) is received through one or more gas-permeable sections of the enclosure 12. In the illustrated example embodiment, the entire enclosure 12 is made from a gas-permeable material.

The pet bed 10 further includes a backing layer 16 that is attached to the heating layer 11. The backing layer 16 restricts movement of the pet bed 10 relative to a surface where the pet bed 10 is situated.

In the embodiment illustrated in FIG. 5, the backing layer 16 and the heating layer 11 are the same size such that the backing layer 16 may be bonded around its perimeter to the perimeter of the enclosure 12 by such means as adhesion, melt-bonding or sewing (among others). It should be noted that the heating layer 11 and the backing layer 16 may be bonded at other locations besides their perimeters, especially when the heating layer 11 and the backing layer 16 are different sizes.

The backing layer 16 may be made from a material that is moisture-proof, comfortable, non-toxic, low cost and/or hygienic. As an example, the backing layer 16 may include a material having a relatively high coefficient of friction such that the material restricts movement of the pet bed 10 relative to a surface where the pet bed 10 is situated. In addition, the backing layer 16 may be textured or patterned to further help restrict movement of the pet bed 10. In some embodiments, the backing layer 16 may be treated with an adhesive (not shown) that increases the coefficient of friction of the backing layer 16.

Some example materials that may be used for backing layer 16 include rubber, plastic, nonwovens, plastic films and PVC (among other materials). In some embodiments, the backing layer 16 may be made from a combination of materials and/or formed of multiple layers that are made of the same material or different materials.

Figure 6:
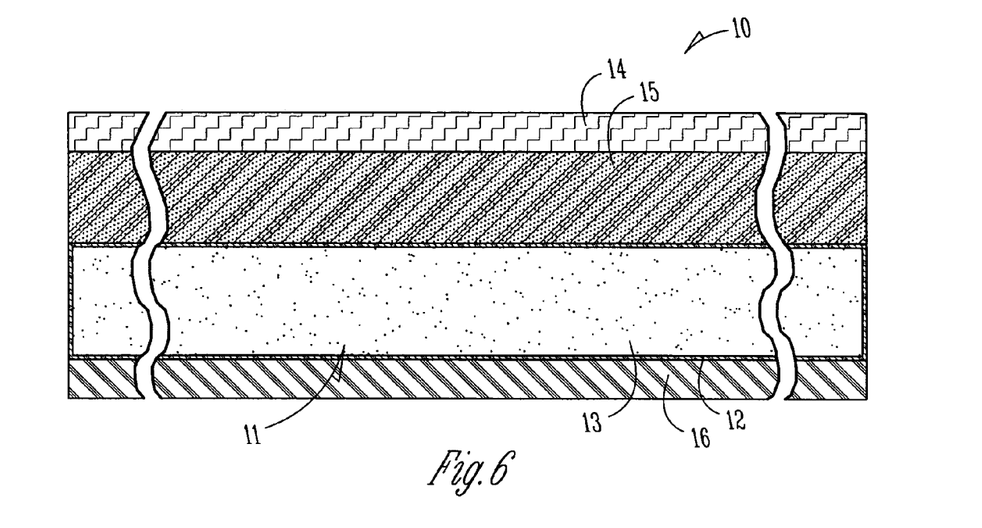
FIG. 6 is a section view that is similar to FIGS. 3–5 illustrating another example embodiment of the pet bed shown in FIG. 2.

FIG. 6 illustrates another example embodiment for pet bed 10. The pet bed 10 includes a heating layer 11 that is formed of an enclosure 12 and a heating composition 13 sealed inside the enclosure 12. The heating composition 13 generates heat when a gas (e.g., air) is received through one or more gas-permeable sections of the enclosure 12. In the illustrated example embodiment, the entire enclosure 12 is made from a gas-permeable material.

The pet bed 10 further includes a liner 14, a conforming layer 15 and a backing layer 16. The conforming layer 15 is attached to the heating layer 11 such that the conforming layer 15 is between the heating layer 11 and the liner 14. The backing layer 16 is attached to the heating layer 11 such that the backing layer 16 is on an opposing side of the heating layer 11 to the conforming layer 15 and the liner 14.

The conforming layer 15 conforms to the shape of a pet and the liner 14 engages the pet as the pet lies on the pet bed 10. In addition, the backing layer 16 restricts movement of the pet bed 10 relative to a surface where the pet bed 10 is situated.

In the example embodiment illustrated in FIG. 6, liner 14, conforming layer 15, backing layer 16 and heating layer 11 are the same size such that each of the liner/layers 14, 15, 16 may be bonded around their perimeters to the perimeter of the enclosure 12 by such means as adhesion, melt-bonding or sewing (among others). It should be noted that the heating layer 11 and the liner/layers 14, 15, 16 may be bonded at other locations besides their perimeters, especially when the heating layer 11 and any of the other liner/layers 14, 15, 16 are different sizes. In addition, the heating layer 11 and the liner/layers 14, 15, 16 may be stacked in other configurations.

It should be noted that one or more of the liner 14, conforming layer 15 and backing layer 16 may form part, or all, of the enclosure 12. As examples, the enclosure 12 may be formed by the backing layer 16 in combination with the liner 14 and/or the conforming layer 15.

Figure 7:
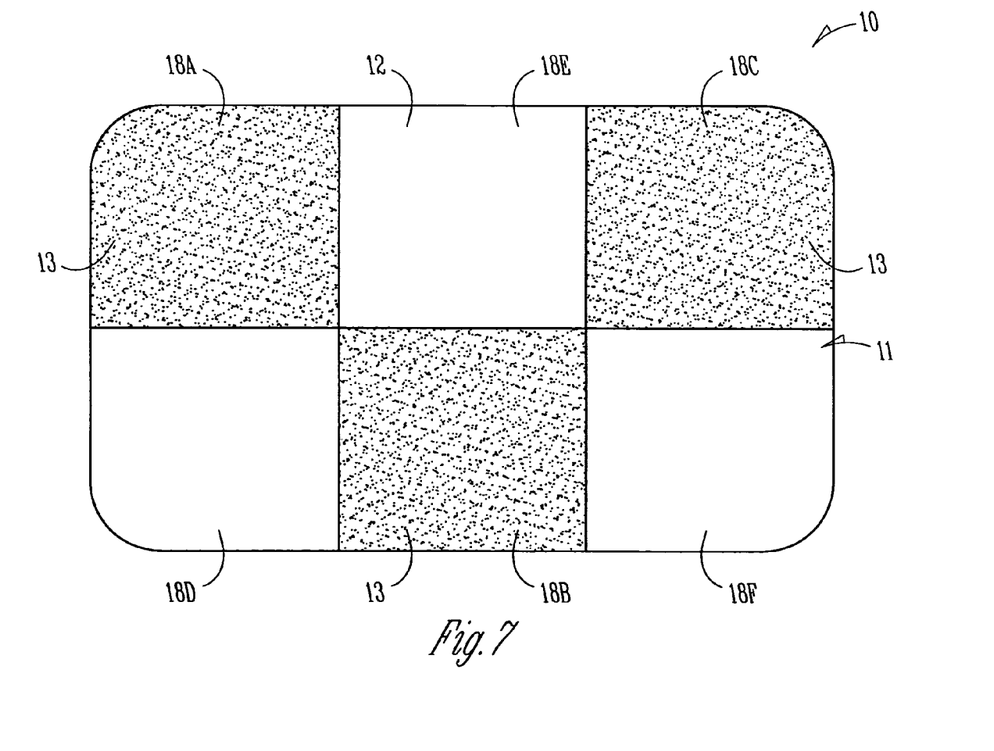
FIG. 7 is a section view illustrating an example embodiment of the pet bed shown in FIG. 3 taken along line 7—7.

FIG. 7 illustrates an example embodiment of the pet bed 10 where the enclosure 12 of the heating layer 11 includes a plurality of sections 18A-18F such that the heating composition 13 is in at least one of the sections 18A-18F. In the example embodiment illustrated in FIG. 7, there is a heating composition 13 in three sections 18A–C out of a total of six sections 18A-18F in the enclosure 12.

It should be noted that the sections 18A-18F may take a variety of forms (e.g., circle, square, rectangle and polygon). In addition, the number size and arrangement of any sections in the enclosure 12 may vary depending on the properties that are desired within the pet bed 10.

Figure 8:
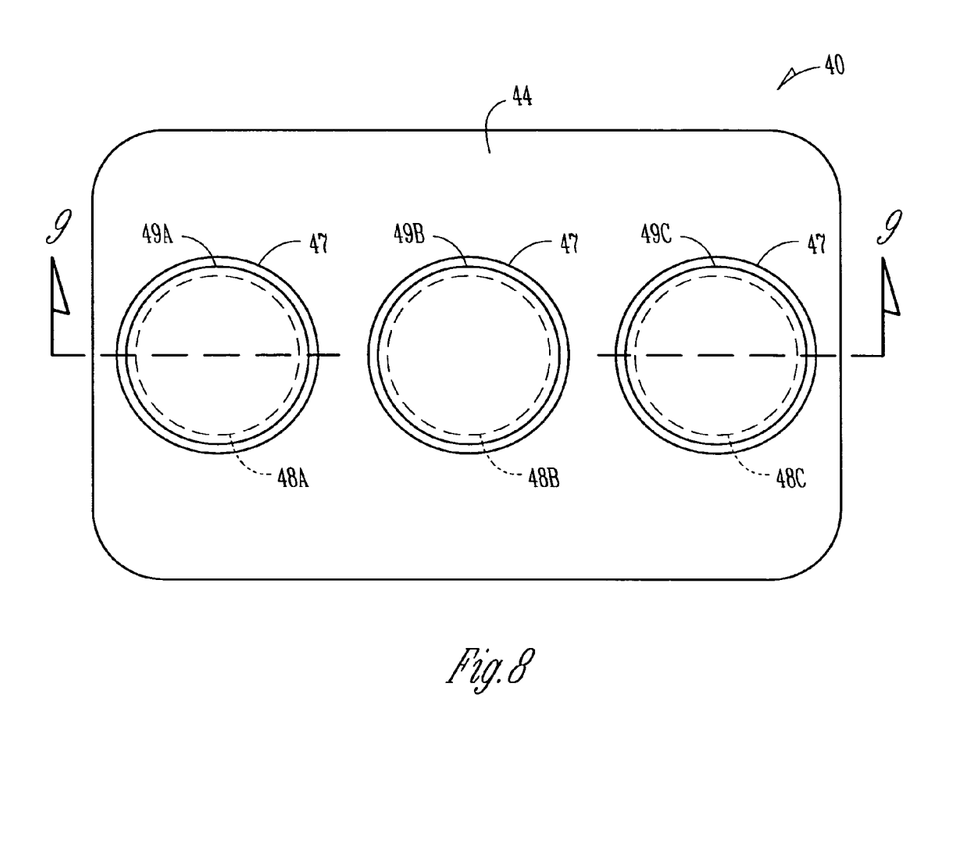
FIG. 8 illustrates a top view of another example pet bed.
Figure 9:
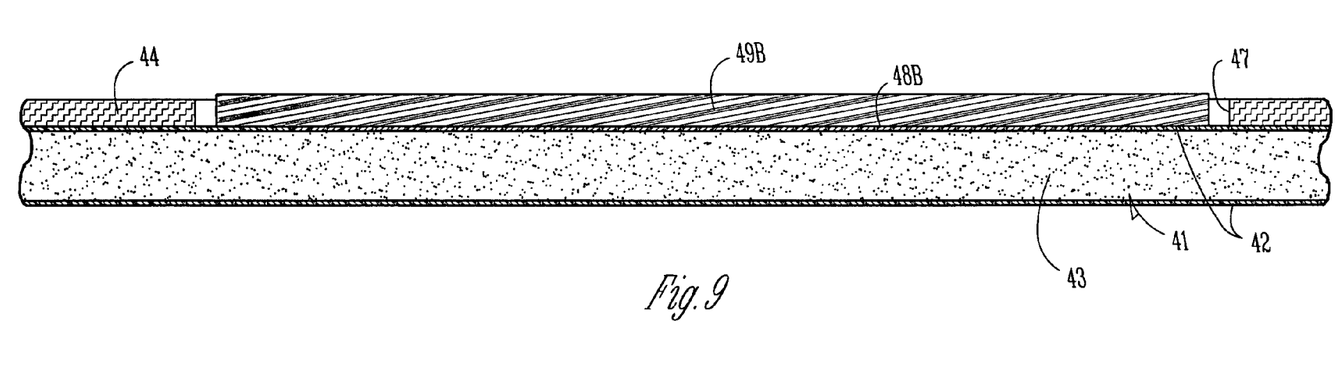
FIG. 9 is a section view illustrating part of the pet bed shown in FIG. 8 taken along line 9—9.
Figure 10:
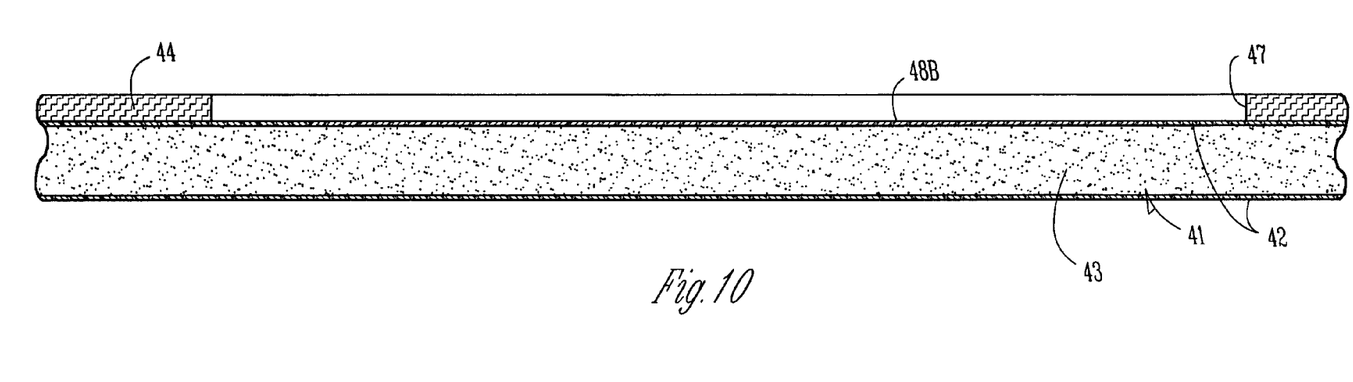
FIG. 10 is a section view similar to FIG. 9 where covers have been removed from an enclosure of the pet bed shown in FIG. 9.

FIGS. 8–10 illustrate another example pet bed 40. The pet bed 40 includes a heating layer 41 that is formed of an enclosure 42 and a heating composition 43 sealed inside the enclosure 42. The pet bed 40 further includes a liner 44 that is attached to the heating layer 41 to engage a pet as the pet lies on the pet bed 40.

FIGS. 8 and 9 show the enclosure 42 as including one or more gas-permeable sections 48A–C and one or more gas-impermeable covers 49A–C that are detachably mounted to an outer surface of the enclosure 42 over the gas-permeable sections 48A–C (see, e.g., cover 49B in FIG. 9). The heating composition 43 (not visible in FIG. 8) is sealed inside the enclosure 42 such that the heating composition 43 generates heat when the gas-impermeable covers 49A–C are removed (FIG. 10) from the enclosure 42 and a gas (e.g., air) is received through the gas-permeable sections 48A–C of the enclosure 42.

The liner 44 includes openings 47 that are aligned with the gas-permeable sections 48A–C and the gas-impermeable covers 49A–C. In some embodiments, the gas-impermeable covers 49A–C are at least partially within the openings 47.

In the example illustrated pet bed 40, the gas-permeable sections 48A–C and the gas-impermeable covers 49A–C are circular. It should be noted that the number, size and shape of the gas-permeable sections 48A–C and the gas-impermeable covers 49A–C may vary depending on the properties that are desired within the pet bed 10.

The gas-impermeable covers 49A–C may be a polyethylene film or any other material that limits or blocks air permeability. In addition, the gas-impermeable covers 49A–C may include an adhesive on one side that releasably engages the outer surface of the enclosure 42.

It should be noted that the pet bed 40 may also include a conforming layer (not shown in FIGS. 8–10) that conforms to the shape of a pet as the pet lies on the pet bed 40, and/or a backing layer (not shown in FIGS. 8–10) that restricts movement of the pet bed 40 relative to a surface where the pet bed 40 is situated. In some embodiments, the pet bed 40 may include a conforming layer and/or a backing layer instead of a liner 44. In addition, the liner 44 may be positioned on an opposing side of the heating layer 41 to any of the gas-permeable sections 48A–C such that the liner 44 does not need to include openings 47.

The covers 49A–C may not all be removed at one time such that the rate of the exothermic reaction is slowed. It should be noted that slowing the exothermic reaction of the heating composition 43 extends the life of the heating composition 43 while reducing the maximum temperature that can be achieved by the pet bed 40. The appropriate rate of the exothermic reaction will depend on the desired properties of the pet bed 40.

FIGS. 1–10 are representational and are not necessarily drawn to scale. Certain proportions thereof may be exaggerated, while others may be minimized.

The pet beds described herein allow an individual to apply heat to a pet over a relatively long period of time without using electricity. The temperature of the pet beds is also easily regulated by controlling the rate of the exothermic reaction that takes place within the pet bed.

While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

We claim:

1. A pet bed comprising:
a heating layer that includes an enclosure and a heating composition sealed inside the enclosure, the enclosure including at least one gas-permeable section and a cover removably attached to an outer surface of the enclosure and surrounding a perimeter of the gas-permeable section such that the heating composition generates heat when the cover is removed from the enclosure and a gas is received through the gas-permeable section of the enclosure; and
a liner attached to the heating layer to engage a pet as the pet lies on the pet bed, wherein the liner has an opening formed therein, said opening being sized such that a perimeter of the cover is located within the opening in the liner.

2. The pet bed of claim 1 wherein the heating composition includes iron powder.

3. The pet bed of claim 1 wherein the enclosure includes a plurality of gas-permeable sections such that a separate cover is positioned over each of the gas-permeable sections of the enclosure.

4. The pet bed of claim 3 wherein each cover is removably attached to the outer surface of the enclosure and surrounds a perimeter of a gas-permeable section such that the heating composition generates heat when at least one cover is removed from the enclosure and a gas is received through at least one of the gas-permeable sections of the enclosure.

5. The pet bed of claim 1 wherein the enclosure is polyethylene.

6. The pet bed of claim 1 further comprising a conforming layer attached to the heating layer, the conforming layer conforming to the shape of a pet as the pet lies on the pet bed.

7. The pet bed of claim 6 wherein the conforming layer is foam.

8. The pet bed of claim 6 wherein a perimeter of the conforming layer is substantially aligned with a perimeter of the liner such that the perimeter of the conforming layer engages the perimeter of the liner.

9. The pet bed of claim 1 further comprising a backing layer attached to the heating layer on an opposing side of the heating layer to the liner, the backing layer restricting movement of the pet bed relative to a surface where the pet bed is situated.

10. The pet bed of claim 9 wherein the backing layer has a higher coefficient of friction than the heating layer.

11. The pet bed of claim 10 wherein the backing layer is textured.

12. The pet bed of claim 1 wherein the enclosure of the heating layer includes a plurality of sections such that the heating composition is in at least one of the sections.

13. The pet bed of claim 1 wherein the liner is nonwoven.

14. The pet bed of claim 1 wherein a perimeter of the heating layer is substantially aligned with a perimeter of the liner such that the perimeter of the heating layer engages the perimeter of the liner.

15. A pet bed comprising:
a heating layer that includes an enclosure and a heating composition sealed inside the enclosure, the enclosure including at least one gas-permeable section and a cover removably attached to an outer surface of the enclosure and surrounding a perimeter of the gas-permeable section such that the heating composition generates heat when the cover is removed from the enclosure and a gas is received though the gas-permeable section of the enclosure;
a liner attached to the heating layer to engage a pet as the pet lies on the pet bed, wherein the liner has an opening formed therein, said opening being sized such that a perimeter of the cover is located within the opening in the liner;
a conforming layer attached to the heating layer, the conforming layer conforming to the shape of a pet as the pet lies on the pet bed; and
a backing layer attached to the conforming layer such that the conforming layer is between the backing layer and the heating layer, the backing layer restricting movement of the pet bed relative to a surface where the pet bed is situated.

16. The pet bed of claim 15 wherein the heating composition includes iron powder.

17. The pet bed of claim 15 wherein the enclosure is polyethylene.

18. The pet bed of claim 15 wherein the enclosure of the heating layer includes a plurality of sections such that the heating composition is in at least one of the sections.

19. The pet bed of claim 15 wherein the conforming layer is foam.

20. The pet bed of claim 15 wherein the liner is nonwoven.

* * * * *